United States Patent [19]

Kleinman

[11] Patent Number: 5,716,967
[45] Date of Patent: Feb. 10, 1998

[54] ISOXAZOLINE COMPOUNDS AS ANTIINFLAMMATORY AGENTS

[75] Inventor: Edward Fox Kleinman, Stonington, Conn.

[73] Assignee: Pfizer Inc., New York, N.Y.

[21] Appl. No.: 640,944

[22] PCT Filed: Oct. 26, 1994

[86] PCT No.: PCT/IB94/00333

§ 371 Date: May 15, 1996

§ 102(e) Date: May 15, 1996

[87] PCT Pub. No.: WO95/14681

PCT Pub. Date: Jun. 1, 1995

Related U.S. Application Data

[63] Continuation-in-part of Ser. No. 262,086, Jun. 17, 1994, abandoned, which is a continuation-in-part of Ser. No. 157,248, Nov. 26, 1993, abandoned.

[51] Int. Cl.$^6$ .................... C07D 261/04; A61K 31/42
[52] U.S. Cl. .................... 514/313; 514/378; 514/379; 546/176; 548/240; 548/241; 548/245
[58] Field of Search .................... 514/313, 378, 514/379; 546/176; 548/240, 241, 245

[56] References Cited

U.S. PATENT DOCUMENTS

| 4,731,382 | 3/1988  | Zusi et al.    | 514/575 |
|-----------|---------|----------------|---------|
| 4,889,551 | 12/1989 | Oda et al.     | 504/271 |
| 5,059,614 | 10/1991 | Lepage et al.  | 514/378 |
| 5,258,397 | 11/1993 | Lepage et al.  | 514/380 |
| 5,273,989 | 12/1993 | Schwab et al.  | 514/378 |

FOREIGN PATENT DOCUMENTS

| 0378991   | 7/1990  | European Pat. Off. |
| 55-104273 | 2/1979  | Japan .             |
| 9108202   | 6/1991  | WIPO .              |
| 9219594   | 11/1992 | WIPO .              |
| 9219589   | 11/1992 | WIPO .              |
| 9402448   | 2/1994  | WIPO .              |
| 9410118   | 5/1994  | WIPO .              |
| 9418158   | 8/1994  | WIPO .              |

OTHER PUBLICATIONS

Gottlieb, M.S. et al. (ed.), "Current Topics in AIDS: vol. 1", John Wiley & Sons, 1988, pp. 51–55.
CA 71:124413, corresponding to GB patent 1,164,510, "Analgesic isoxazole derivatives", Inperial Chemical Industries Ltd., 1969.
Chemical Abstracts 71:124413x "Analgesic Isoxazole Derivatives", p. 460, 1969.
CA 112: 198215w, p. 699, 1990.
CA 112: 216875t, pp. 639–640, 1990.
Database WPI Week 9145, Derwent Publications Ltd., London, GB; AN 91–329223 & JP, A, 3 220 180 (Taiho Pharm. K.K.) 27. Sep. 1991, see abstract.
Arzneim.–Forsch., vol. 24, No. 4, 1974, pp. 494–499.
J. Org. Chem., vol. 37, No. 19, 1972, Tuman et al., pp. 2983–2986.

*Primary Examiner*—C. Warren Ivy
*Assistant Examiner*—Lyman H. Smith
*Attorney, Agent, or Firm*—Peter C. Richardson; Gregg C. Benson

[57] ABSTRACT

This invention relates to isoxazoline compounds which are selective inhibitors of phosphodiesterase type IV ($PDE_{IV}$). The isoxazoline compounds are useful in inhibiting $PDE_{IV}$ and in the treatment of AIDS, asthma, arthritis, bronchitis, chronic obstructive pulmonary disease, psoriasis, allergic rhinitis, dermatitis, shock, atopic dermatitis, rheumatoid arthritis and osteoarthritis. This invention also relates to pharmaceutical compositions useful therefor.

16 Claims, No Drawings

ISOXAZOLINE COMPOUNDS AS ANTIINFLAMMATORY AGENTS

CROSS REFERENCE TO RELATED APPLICATIONS

This application is the national stage of International Application No. PCT/IB94/00333, filed Oct. 26, 1994, published as WO/95/14681 on Jun. 1, 1995, designating, inter alia, the United States which is a continuation-in-part of U.S. application Ser. No. 08/262,086, filed Jun. 17, 1994, now abandoned which is a continuation-in-part of U.S. application Ser. No. 08/157,248 filed Nov. 26, 1993, now abandoned.

BACKGROUND OF THE INVENTION

This invention relates to a series of 3-aryl-2-isoxazoline-5-hydroxamic acid compounds which are selective inhibitors of phosphodiesterase type IV ($PDE_{IV}$) and as such are useful in the treatment of AIDS, asthma, arthritis, bronchitis, chronic obstructive pulmonary disease, psoriasis, allergic rhinitis, dermatitis and other inflammatory conditions.

This invention also relates to the pharmaceutically acceptable salts of said compounds; to a method of using such compounds in inhibiting $PDE_{IV}$, and in the treatment of inflammatory conditions, AIDS, asthma, arthritis, bronchitis, chronic obstructive pulmonary disease, psoriasis, allergic rhinitis and dermatitis in mammals, especially humans; and to pharmaceutical compositions useful therefor.

The "inflammatory conditions" which can be treated according to this invention include, but are not limited to, chronic obstructive pulmonary disease, shock, atopic dermatitis, bronchitis, rheumatoid arthritis and osteoarthritis.

Since the recognition that cyclic AMP is an intracellular second messenger (E. W. Sutherland, and T. W. Rall, *Pharmacol. Rev.*, 1960, 12, 265), inhibition of the phosphodiesterases has been a target for modulation and, accordingly, therapeutic intervention in a range of disease processes. More recently, distinct classes of PDE have been recognized (J. A. Beavo and D. H. Reifsnyder, *TIPS*, 1990, 11,150), and their selective inhibition has led to improved drug therapy (C. D. Nicholson, R. A. Challiss and M. Shahid, *TIPS*, 1991, 1:2, 19). More particularly, it has been recognized that inhibition of $PDE_{IV}$ can lead to inhibition of inflammatory mediator release (M. W. Verghese et al., *J. Mol. Cell Cardiol.*, 1989, 12 (Suppl. II), S 61) and airway smooth muscle relaxation (T. J. Torphy in *Directions for New Anti-Asthma Drugs*, eds S. R. O'Donnell and C. G. A, Persson, 1988, 37, Birkhauser-Verlag). Thus, compounds that inhibit $PDE_{IV}$, but which have poor activity against other PDE types, would inhibit the release of inflammatory mediators and relax airway smooth muscle without causing cardiovascular effects or antiplatelet effects.

Certain pyrimidone compounds have been disclosed to be useful as antidepressants by Saccomano et al., in European Patent Application EPO 247 725 A2 published Dec. 2, 1987. The same pyrimidone compounds have been disclosed to be useful against asthma and certain skin disorders in International Patent Application No. PCT/US90/02162, published May 30, 1991 as International Publication Number WO 91/07178.

SUMMARY OF THE INVENTION

This invention is concerned with a series of 3-aryl-2-isoxazoline-5-hydroxamic acid compounds and to the pharmaceutically acceptable salts of such compounds. These new compounds possess inhibitory activity against $PDE_{IV}$ and as such are useful in treating inflammatory conditions, AIDS, asthma, arthritis, bronchitis, chronic obstructive pulmonary disease, psoriasis, allergic rhinitis or dermatitis in a mammal, especially humans.

The compounds of the present invention are of the formula (I)

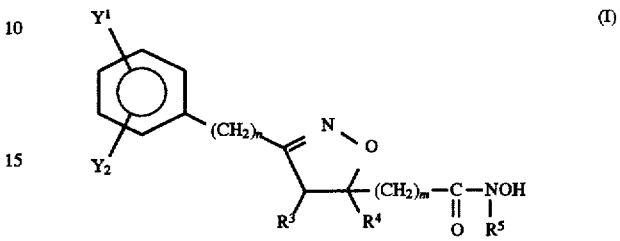

the racemic, racemic-diastereomeric mixtures and optical isomers of said compounds and the pharmaceutically acceptable salts thereof wherein m is 0, 1, 2 or 3;

n is 0, 1, 2 or 3;

$Y^1$ and $Y^2$ are independently selected from the group consisting of hydrogen, ($C_1$–$C_6$)alkyl, optionally substituted phenylalkyl having 1 to 6 carbons in the alkyl portion, optionally substituted phenoxyalkyl having 1 to 6 carbons in the alkyl portion, ($C_3$–$C_7$)cycloalkyl, difluoromethyl, trifluoromethyl, fluoro, chloro, bromo, iodo, —$OR^1$ and —$OR^2$;

wherein the aromatic portion of the optionally substituted phenylalkyl, and the aromatic portion of the optionally substituted phenoxyalkyl are optionally independently substituted with ($C_1$–$C_4$)alkyl, ($C_1$–$C_4$)alkoxy, halogen or $CF_3$; $R^1$ is ($C_1$–$C_4$)alkyl, phenylalkyl having one to four carbon atoms in the alkyl portion fluoromethyl, difluoromethyl, trifluoromethyl, or —$(CH_2)_q$-quinoline wherein q is 1,2 or 3;

$R^2$ is ($C_1$–$C_3$alkyl, ($C_3$–$C_7$)cycloalkyl, alkoxyalkyl having 3 to 7 carbons in the alkoxy portion and 2 to 4 carbons in the alkyl portion, optionally substituted phenoxyalkyl having 2 to 6 carbons in the alkyl portion, optionally substituted phenylalkyl having 1 to 6 carbons in the alkyl portion, bicycloalkyl having 6 to 9 carbons or optionally substituted indanyl;

wherein the aromatic portion of the optionally substituted phenylalkyl, the aromatic portion of the optionally substituted phenoxyalkyl and the optionally substituted indanyl are optionally substituted with ($C_1$–$_4$)alkyl, ($C_1$–$_4$)alkoxy, halogen or $CF_3$;

$R^3$ is hydrogen, ($C_1$–$C_3$)alkyl, fluoro($C_1$–$C_3$)alkyl having 1 to 3 fluoro atoms, mono-hydroxyalkyl having 1 to 3 carbons or alkoxyalkyl having 1 to 3 carbons in the alkyl portion and 1 to 3 carbons in the alkoxy portion;

$R^4$ is hydrogen, ($C_1$–$C_5$)alkyl, fluoro($C_1$–$C_5$)alkyl having 1 to 3 fluoro atoms, mono-hydroxyalkyl having 1 to 3 carbons, phenyl, alkoxyalkyl having 1 to 3 carbons in the alkyl portion and 1 to 3 carbons in the alkoxy portion, aminoalkyl having 1 to 3 carbons,

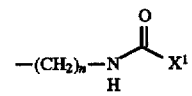

wherein $X^1$ is ($C_1$–$C_3$) alkyl and n is an integer from 1 to 3, N-alkylaminoalkyl having 1 to 3 carbons in the alkylamino portion and 1 to 3 carbons in the alkyl portion, ($C_3$–$C_7$) cycloalkyl or N,N-dialkylaminoalkyl having a total of 2 to 6 carbons in the dialkylamino portion and 1 to 3 carbons in the alkyl portion; $R^5$ is hydrogen or ($C_1$–$C_3$)alkyl;

or $R^3$ and $R^4$ are taken together with the carbon atoms to which they are attached and form a carbocyclic ring having 4 to 7 carbon atoms.

A preferred group of compounds or the pharmaceutically acceptable salts thereof are those compounds of the formula (I) wherein $Y^1$ is —$OR^1$ and is attached to the 4-position of the phenyl ring; $Y^2$ is —$OR^2$ and is attached to the 3-position of the phenyl ring and m, n, $R^1$, $R^2$, $R^3$, $R^4$ and $R^5$ are as defined above for formula (I).

A more preferred group of compounds or the pharmaceutically acceptable salts thereof are those compounds of the formula (I) wherein $Y^1$ is —$OR^1$ and is attached to the 4-position of the phenyl ring and $Y^2$ is —$OR^2$ and is attached to the 3-position of the phenyl ring wherein $R^1$ is ($C_1$–$C_4$)alkyl, phenylalkyl having one to four carbon atoms in the alkyl portion or —$(CH_2)_q$-quinoline; m is 0; n is 0; and $R^2$, $R^3$, $R^4$ and $R^5$ are as defined above for formula (I).

Another more preferred group of compounds or the pharmaceutically acceptable salts thereof are those compounds of the formula (I) wherein $Y^1$ is —$OR^1$ and is attached to the 4-position of the phenyl ring and $Y^2$ is —$OR^2$ and is attached to the 3-position of the phenyl ring wherein $R^1$ Is ($C_1$–$C_4$)alkyl, phenylalkyl having one to four carbon atoms in the alkyl portion or -$(CH_2)_q$-quinoline; $R^2$ is phenylalkyl having 1 to 6 carbons in the alkyl portion, ($C_3$–$C_7$)cycloalkyl, or ($C_1$l)alkyl; m is 0; n is 0; and $R^3$, $R^4$ and $R^5$ are as defined above for formula (I).

An even more preferred group of compounds or the pharmaceutically acceptable salts thereof are those compounds of the formula (I) wherein $Y^1$ is —$OR^1$ and is attached to the 4-position of the phenyl ring and $Y^2$ is —$OR^2$ and is attached to the 3-position of the phenyl ring wherein $R^1$ is ($C_1$–$C_4$)alkyl, phenylalkyl having one to four carbon atoms in the alkyl portion or —$(CH_2)_q$-quinoline; $R^2$ is 5-phenylpentyl, benzyl, cyclopentyl or methyl; m is 0; n is 0; and $R^3$, $R^4$ and $R^5$ are as defined above for formula (I).

A particularly preferred group of compounds or the pharmaceutically acceptable salts thereof are those compounds of the formula (I) wherein $Y^1$ is —$OR^1$ and is attached to the 4-position of the phenyl ring and $Y^2$ is —$OR^2$ and is attached to the 3-position of the phenyl ring wherein $R^1$ is ($C_1$–$C_4$)alkyl, phenylalkyl having one to four carbon atoms in the alkyl portion or —$(CH_2)_q$-quinoline; $R^2$ is 5-phenylpentyl, benzyl, cyclopentyl or methyl; m is 0; n is 0; $R^3$ is hydrogen and $R^4$ and $R^5$ are as defined above for formula Another particularly preferred group of compounds or the pharmaceutically acceptable salts thereof are those compounds of the formula (I) wherein $Y^1$ is —$OR^1$ and is attached to the 4-position of the phenyl ring and $Y^2$ is —$OR^2$ and is attached to the 3-position of the phenyl ring wherein $R^1$ is ($C_1$–$C_4$)alkyl, phenylalkyl having one to four carbon atoms in the alkyl portion or —$(CH_2)_q$-quinoline; $R^2$ is 5-phenylpentyl, benzyl, cyclopentyl or methyl; m is 0; n is 0; $R^3$ is hydrogen; $R^4$ is hydrogen or ($C_1$–$C_5$) alkyl and $R^5$ is as defined above for formula (I).

A more particularly preferred group of compounds or the pharmaceutically acceptable salts thereof are those compounds of the formula (I) wherein $Y^1$ is —$OR^1$ and is attached to the 4-position of the phenyl ring and $Y^2$ is —$OR^2$ and is attached to the 3-position of the phenyl ring wherein $R^1$ is ($C_1$–$C_4$)alkyl, phenylalkyl having one to four carbon atoms in the alkyl portion or —$(CH_2)_q$-quinoline; $R^2$ is 5-phenylpentyl, benzyl, cyclopentyl or methyl; m is 0; n is 0; $R^3$ is hydrogen; $R^4$ is hydrogen or ($C_1$–$C_5$)alkyl and $R^5$ is hydrogen or ($C_1$–$C_3$)alkyl; a compound or the pharmaceutically acceptable salt thereof of the formula (I) wherein $Y^1$ is —$OR^1$ and is attached to the 4-position of the phenyl ring and $Y^2$ is —$OR^2$ and is attached to the 3-position of the phenyl ring wherein $R^1$ is methyl; $R^2$ is cyclopentyl; m is 0; n is 0; $R^3$ is hydrogen; $R^4$ is hydrogen; and $R^5$ is hydrogen; and the levorotatory (negative rotation) isomer of a compound or the pharmaceutically acceptable salt thereof of the formula (I) wherein $Y^1$ is —$OR^1$ and is attached to the 4-position of the phenyl ring and $Y^2$ is —$OR^2$ and is attached to the 3-position of the phenyl ring wherein $R^1$ is methyl; $R^2$ is cyclopentyl; m is 0; n is 0; $R^3$ is hydrogen; $R^4$ is hydrogen; and $R^5$ is hydrogen.

Another more particularly preferred group of compounds or the pharmaceutically acceptable salts thereof are those compounds of the formula (I) wherein $Y^1$ is —$OR^1$ and is attached to the 4-position of the phenyl ring and $Y^2$ is —$OR^2$ and is attached to the 3-position of the phenyl ring wherein $R^1$ is methyl; $R^2$ is cyclopentyl; m is 0; n is 0; $R^3$ is hydrogen; $R^4$ is methyl; and $R^5$ is hydrogen; and the levorotatory (negative rotation) isomer of a compound or the pharmaceutically acceptable salt thereof of the formula (I) wherein $Y^1$ is —$OR^1$ and is attached to the 4-position of the phenyl ring and $Y^2$ is —$OR^2$ and is attached to the 3-position of the phenyl ring wherein $R^1$ is methyl; $R^2$ is cyclopentyl; m is 0; n is 0; $R^3$ is hydrogen; $R^4$ is methyl; and $R^5$ is hydrogen.

The term alkyl encompasses both straight and branched chains. The aromatic portion of the optionally substituted phenylalkyl, the aromatic portion of the optionally substituted phenoxyalkyl and the optionally substituted indanyl may be substituted by one or more substituents.

DETAILED DESCRIPTION OF THE INVENTION

The compounds of the present invention having the formula (I) are comprised of the racemic, racemic-diastereomeric mixtures and optical isomers of said compounds and the pharmaceutically acceptable salts thereof. The compounds of the present invention, having the formula I as defined above, are readily and generally prepared by the following reaction process.

To an alcoholic solution of sodium methoxide is added an alcoholic solution of hydroxylamine hydrochloride and a compound of the formula

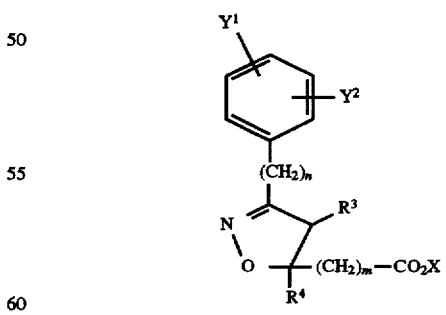

wherein $Y^1$, $Y^2$, $R^3$, $R^4$, m and n are as defined above for the compound of formula (I), and X is an alkyl group. The reaction mixture is stirred for about 12 to 24 hours, preferably 16 hours, at room temperature. The solvent is evaporated and the residue is worked-up according to methods well known to those skilled in the art.

The intermediate ester compounds of the formula

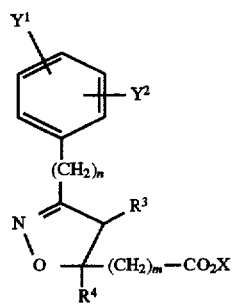

wherein $Y^1$, $Y^2$, $R^3$, $R^4$, m and n are as defined above for the compound of formula (I), and X is an alkyl group, are synthesized according to the following procedure. To a mixture of N-chlorosuccinimide and pyridine in an inert solvent, such as methylene chloride, is added an oxide of the formula

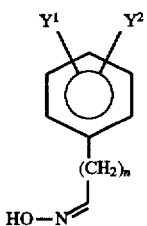

wherein $Y^1$ and $Y^2$ are as defined above for formula (I). The mixture is allowed to stir for about 2 to 5 hours, preferably about 2 hours. A compound of the formula

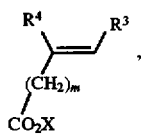

wherein $R^3$ and $R^4$ are as defined above for formula I and X is an alkyl group, is added followed by the addition of triethylamine to the mixture and the mixture stirred for about 2 hours more at room temperature. The reaction is worked up according to methods well known to those skilled in the art.

The synthetic method outlined above together with the following examples describe methods which were and can be employed to prepare the compounds of this invention.

Where possible, as ascertained by one skilled in the art enabled by this disclosure, pharmaceutically-acceptable acid addition salts of certain compounds of this invention include, but are not limited to, those formed with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartaric acid, maleic acid and succinic acid. In the case of those compounds of the formula (I) which contain a further basic nitrogen, it will, of course, be possible to form diacid addition salts (e.g., the dihydrochloride) as well as the usual monoacid addition salt. Where possible, as ascertained by one skilled in the art enabled by this disclosure, pharmaceutically-acceptable cationic salts of certain compounds of this invention include, but are not limited to, those of sodium, potassium, calcium, magnesium, ammonium, N,N'-dibenzylethylenediamine, N-methylglucamine (meglumine), ethanolamine and diethanolamine.

The starting materials and reagents required for the synthesis of the compounds of the present invention are readily available, either commercially, according to literature methods, or by methods exemplified in Preparations below.

The ability of the compounds or the pharmaceutically acceptable salts thereof to inhibit $PDE_{IV}$ and, consequently, demonstrate their effectiveness for treating inflammatory conditions is shown by the following in vitro assays.

BIOLOGICAL ASSAYS

Human Lung $PDE_{IV}$

Thirty to forty grams of human lung tissue is placed in 50 mL of pH 7.4 Tris/phenylmethylsulfonyl fluoride (PMSF)/sucrose buffer and homogenized using a Tekmar Tissumizer® (Tekmar Co., 7143 Kemper Road, Cincinnati, OH 45249) at full speed for 30 seconds. The homogenate is centrifuged at 48,000×g for 70 minutes at 4° C. The supernatant is filtered twice through a 0.22 μm filter and applied to a Mono-Q FPLC column (Pharmacia LKB Biotechnology, 800 Centennial Avenue, Piscataway, NJ 08854) pre-equilibrated with pH 7.4 Tris/PMSF buffer. A flow rate of 1 mL/minute is used to apply the sample to the column, followed by a 2 mL/minute flow rate for subsequent washing and elution. Sample is eluted using an increasing, step-wise NaCl gradient in the pH 7.4 Tris/PMSF buffer. Eight mL fractions are collected. Fractions are assayed for specific $PDE_{IV}$ activity, determined by [$^3$H]cAMP hydrolysis and the ability of a known $PDE_{IV}$ inhibitor (e.g. rolipram) to inhibit that hydrolysis. Appropriate fractions are pooled, diluted with ethylene glycol (2 mL ethylene glycol/5 mL of enzyme prep) and stored at −20° C. until use.

Compounds are dissolved in DMSO at a concentration of 10 mM and diluted 1:25 in water (400 μM compound, 4% DMSO). Further serial dilutions are made in 4% DMSO to achieve desired concentrations. Final DMSO concentration in the assay tube is 1%. In duplicate the following are added, in order, to a 12×75 mm glass tube (all concentrations are given as final concentrations in assay tube).

i) 25 μl compound or DMSO (1%, for control and blank)
ii) 25 μl pH 7.5 Tris buffer
iii) [$^3$H]cAMP (1 μM)
iv) 25 μl $PDE_{IV}$ enzyme (for blank, enzyme is preincubated in boiling water for 5 minutes)

The reaction tubes are shaken and placed in a water bath (37° C.) for 20 minutes, at which time the reaction is stopped by placing the tubes in a boiling water bath for 4 minutes. Washing buffer (0.5 mL, 0.1 M 4-(2-hydroxyethyl)-1-piperazineethanesulfonic acid (HEPES)/0.1 M NaCl, pH 8.5) is added to each tube on an ice bath. The contents of each tube are applied to an Aft-Gel 601 column (Biorad Laboratories, P.O. Box 1229, 85A Marcus Drive, Melville, New York 11747) (boronate affinity gel, 1 mL bed volume) previously equilibrated with washing buffer. [$^3$H]cAMP is washed with 2×6 mL washing buffer, and [$^3$H]5'AMP is then eluted with 4 mL of 0.25 M acetic acid. After vortexing, 1 mL of the elution is added to 3 mL of scintillation fluid in a suitable vial, vortexed and counted for [$^3$H].

Inhibition is determined by the formula:

$$\% \text{ inhibition} = 1 - \frac{\text{average } cpm \text{ (test compound)} - \text{average } cpm \text{ (blank)}}{\text{average } cpm \text{ (control)} - \text{average } cpm \text{ (blank)}} \times 100$$

$IC_{50}$ is defined as that concentration of compound which inhibits 50% of specific hydrolysis of [$^3$H]cAMP to [$^3$H]5'AMP.

For administration to humans to inhibit PDE$_{IV}$ and in the treatment of inflammatory conditions, AIDS, asthma, arthritis, bronchitis, chronic obstructive pulmonary disease, psoriasis, allergic rhinitis or dermatitis, oral dosages of the compounds of formula (I) or the pharmaceutically acceptable salts thereof, are generally in the range of from 0.1–500 mg daily for an average adult patient (70 kg). Thus for a typical adult patient, individual tablets or capsules contain from 0.1 to 50 mg of active compound, in a suitable pharmaceutically acceptable vehicle or carrier. Multiple tablets or capsules may be required to meet the dosage requirements. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the compounds of the formula (I) and the pharmaceutically acceptable salts thereof can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic. For topical administration, they are best used in the form of solutions, lotions, ointments, salves and the like.

Thus in a further aspect the invention provides pharmaceutical compositions comprising a compound of the formula (I), or a pharmaceutically acceptable salts thereof, together with a pharmaceutically acceptable diluent or carrier which are useful; in inhibiting PDE$_{IV}$; in the treatment of inflammatory conditions and in the treatment of AIDS, asthma, arthritis, bronchitis, chronic obstructive pulmonary disease, psoriasis, allergic rhinitis and dermatitis in mammals, especially humans.

This invention also provides methods of inhibiting PDE$_{IV}$ in a mammal in need thereof which methods comprise administering to said mammal a PDE$_{IV}$ inhibiting amount of a compound of the formula (I) or a pharmaceutically acceptable salt thereof.

This invention further provides a method of treating an inflammatory condition in a mammal in need thereof which comprises administering to said mammal an antiinflammatory amount of a compound of the formula (I) or a pharmaceutically acceptable salt thereof.

Further still, this invention provides a method of treating AIDS, asthma, arthritis, bronchitis, chronic obstructive pulmonary disease, psoriasis, allergic rhinitis, dermatitis or shock in a mammal in need thereof which comprises administering to said mammal an effective amount of a compound or a pharmaceutically acceptable salt thereof.

The present invention is illustrated by the following examples, but it is not limited to the details thereof.

EXAMPLE 1

3-(3-Cyclopentyloxy-4-methoxy)phenyl-2-isoxazoline-5-hydroxamic Acid

To a solution of sodium methoxide, prepared from 97 mg (4.2 mmol) of sodium and 10 mL of methanol, was added 146 mg (2.1 mmol) of hydroxylamine hydrochloride in a solution of 3 mL of methanol followed by 500 mg (1.5 mmol) of the compound of Preparation 10. After stirring for about 16 h at RT, the solvent was evaporated and the residue was dissolved in 50 mL of water and washed with ether (2×50 mL). The aqueous layer was acidified to pH 1 with aqueous HCl solution and the precipitate (231 mg) was filtered and recrystallized twice from $CH_2Cl_2$/EtOAc to give 52 mg of the title compound, mp 167°–168° C. $^1$H NMR (DMSO-$D_6$): δ 1.54–1.92 (8H, m), 3.48–3.67 (2 Hm), 3.78 (3 H, s), 4.79–4.85 (1 H, m), 4.95 (1 H, t, J=8), 6.99 (1 H, d, J=9), 7.17 (1 H, d, J=9), 7.23 (1 H, s), 9.03 (1 H, s); Anal. Calc'd. for $C_{16}H_{20}N_2O_5$:C, 59.99 ; H, 6.29; N, 8.74. Found: C, 59.82 H, 6.05; N, 8.65.

EXAMPLES 2–16

The following compounds having the formula shown below were prepared substantially according to the procedure of Example 1 substituting the indicated ester for that of the ester of Preparation 10. In the case of Example 5, N-methyl-hydroxylamine hydrochloride was substituted for hydroxylamine hydrochloride.

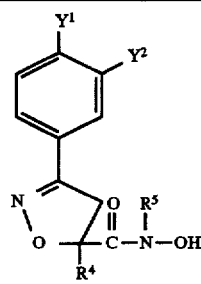

| Ex | Y$^1$ | Y$^2$ | R$^4$ | R$^5$ | Ester | M.P. (°C.) | Data |
|---|---|---|---|---|---|---|---|
| 2 | —OMe | —O(CH$_2$)$_3$Ph | H | H | Cmpd. of Prep 8 | 130–132 | Anal. Calc'd for C$_{22}$H$_{26}$N$_2$O$_5$: C, 66.32; H, 6.58; N, |

-continued

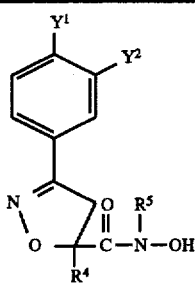

| Ex | Y¹ | Y² | R⁴ | R⁵ | Ester | M.P. (°C.) | Data |
|----|----|----|----|----|-------|-----------|------|
| | | | | | | | 7.03. Found: C, 66.23; H, 6.50; N, 6.94 |
| 3 | —OMe | —O(CH₂)₅Ph | Et | H | Cmpd. of Prep. 9 | 169–171 | Anal. Calc'd for $C_{24}H_{30}N_2O_5 \cdot \frac{1}{4}H_2O$: C, 66.82; H, 7.07; N, 6.49. Found: C, 67.13; H, 7.03; N, 6.15 |
| 4 | —OMe | —O-cyclopentyl | Me | H | Cmpd. of Prep. 12 | 171–173 | Anal. Calc'd for $C_{17}H_{22}N_2O_5 \cdot \frac{1}{2}H_2O$ C, 59.41; H, 6.70; N, 8.15. Found: C, 59.78; H, 6.38; N, 8.27 |
| 5 | —OMe | —O-cyclopentyl | H | Me | Cmpd. of Prep. 11 | 146–148 | Anal. Calc'd for $C_{17}H_{22}N_2O_5$: C, 61.07; H, 6.63; N, 8.38. Found: C, 60.87; H, 6.52; N, 8.45 |
| 6 | —OMe | —OMe | H | H | Cmpd. of Prep. 22 | 180–182 | Anal. Calc'd for $C_{12}H_{14}N_2O_5$: C, 54.13; H, 5.30; N, 10.52. Found: C, 54.03; H, 5.12; N, 10.60 |
| 7 | —OMe | —OCH₂Ph | H | H | Cmpd. of Prep. 23 | 166–168 | Anal. Calc'd for $C_{18}H_{18}N_2O_5$: C, 63.15; H, 5.30; H, 8.18. Found: C, 63.32; H, 5.37; H, 8.09 |
| 8 | quinolin-2-yl-CH₂O— | H | H | H | Cmpd. of Prep. 24 | — | ¹NMR (DMSO-d₆): δ 3.48–3.68 (2H, m), 4.95 (1H, t, J=8), 5.43 (2H, s), 7.15 (2H, d, J=9), 7.59–7.69 (4H, m), 7.80 (1H, t, J=8), 8.01 (2H, t, J=7), 8.42 (1H, d, J=9), 9.04 (1H, s), 10.99 (1H, s). MS (m/e): 363 (M⁺) |
| 9 | —OCH₂Ph | H | H | H | Cmpd. of Prep. 25 | 190–192 | ¹H NMR (DMSO-d₆: δ d 3.44–3.63 (2H, m), 4.94 (1H, t, J=8), 5.15 (2H, s), 7.08 (2H, d, J=8), 7.32–7.46 (5H, m), 7.62 (2H, d, J=8), 9.03(1H, s); MS (m/e): 313 (M⁺ +1) |

-continued

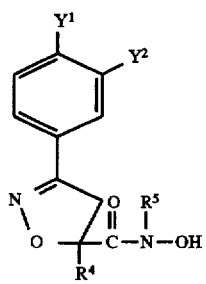

| Ex | Y¹ | Y² | R⁴ | R⁵ | Ester | M.P. (°C.) | Data |
|----|----|----|----|----|-------|-----------|------|
| 10 | H | —O—cyclopentyl | H | H | Cmpd. of Prep. 13 | 151–153 | Anal. Calc'd for $C_{15}H_{18}N_2O_4$: C, 9.65. Found: C, 62.00; H, 6;15; N, 9.36 |
| 11 | —O—cyclopentyl | —OMe | H | H | Cmpd. of Prep. 14 | 136–138 | Anal. Calc'd for $C_{16}H_{20}N_2O_5$: C, 59.99; H, 6.29; N, 8.74. Found: C, 59.66; H, 6.21; N, 8.69 |
| 12 | H | H | H | H | Cmpd. of Prep. 17 | 166–168 | Anal. Calc'd for $C_{10}H_{10}N_2O_3$: C, 58.25; H, 4.89; N, 13.59. Found: C, 58.24; H, 4.49; N, 13.45 |
| 13 | OMe | —O—cyclopentyl | Pr | H | Cmpd. of Prep. 18 | 154–157 | Anal. Calc'd for $C_{19}H_{26}N_2O_5$: C, 62.97; H, 7.23; N, 7.73. Found: C, 62.61; H, 7.19; N, 7.54. |
| 14 | OMe | —O—cyclopentyl | Bu | H | Cmpd. of Prep. 19 | 135–138 | HRMS. Calc'd for $C_{20}H_{28}N_2O_5$: 376.19982. Found: 376.20104. |
| 15 | OMe | —O—cyclopentyl | Ph | H | Cmpd. of Prep. 20 | 180–182 | Anal Calc'd for $C_{22}H_{24}N_2O_5$: C, 7.07. Found: C, 66.32; H, 6.30; N, 7.12. |
| 16 | (structure: 4-OMe, 3-O-cyclopentyl phenyl attached to fused isoxazoline-cyclopentane bearing CONHOH) | | | | Cmpd. of Prep. 21 | 111–133 | HRMS: Calc'd for $C_{19}H_{24}N_2O_5$: 360.1685; Found: 360.1684. |

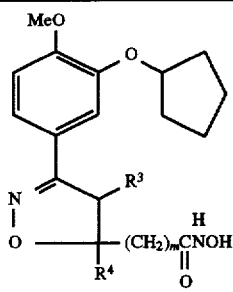

| Example | Ester Cmpd. of Prep. # | R³ | R⁴ | m | MP (°C.) | [α]_D^25 | Anal. |
|---|---|---|---|---|---|---|---|
| 17 | 28 | H | H | 0 | 137–140° | +77° MeOH | Calc'd. for $C_{16}H_{20}N_2O_5$: C, 59.99; H, 6.29; N, 8.74. Found: C, 59.98; H, 6.62; N, 8.80. |
| 18 | 29 | H | H | 0 | 138–140° | –82° MeOH | Calc'd. for $C_{16}H_{20}N_2O_5$: C, 59.99; H, 6.29; N, 8.74. Found: C, 59.66; H, 6.44; N, 8.61. |
| 19 | 33 | H | H | 1 | 139–141° | racemic | Calc'd. for $C_{17}H_{22}N_2O_5 \cdot \frac{1}{4}H_2O$: C, 60.02; H, 6.64; N, 8.26. Found: C, 59.63; H, 6.48; N, 8.15. |
| 20[a] | 31 | Me | H | 0 | 184–186° | racemic | Calc'd. for $C_{17}H_{22}N_2O_5$: C, 61.01; H, 6.58; N, 8.38. Found: C, 61.08; H, 6.88; N, 8.04. |
| 21 | 39 | H | Me | 0 | 167–168° | +9°[b] CHCl₃ | Calc'd. for $C_{17}H_{22}N_2O_5 \cdot \frac{1}{4}H_2O$: C, 60.25; H, 6.69; N, 8.27. Found: C, 60.43; H, 6.70; N, 8.23. |
| 22 | 40 | H | Me | 0 | 153–155° | –14°[b] CHCl₃ | Calc'd. for $C_{17}H_{22}N_2O_5 \cdot \frac{1}{2}H_2O$: C, 59.41; H, 6.70; N, 8.15. Found: C, 59.64; H, 6.65; N, 8.03. |

[a]trans isomer
[b]These compounds are the resolved enantiomers of Example 4. The enantiomeric purity was 99% as determined by chiral HPLC using a ChromTech chiral column. Mobile phase: 98:2 10 mM ammonium acetate buffer, pH 4.1: 2-propanol; flow rate: 1 mL/min; detection: 230 nM; temperature: ambient; injection volume: 20 μL

PREPARATION 1

4-Methoxy-3(5-phenylpentyloxy)benzaldehyde Oxide

A mixture of 25.0 g (0.164 mol) of isovanillin, 26.9 g (0.164 mol) of 5-phenyl-1-pentanol, 64.5 g (0.246 mol) of triphenylphosphine and 250 mL of THF was treated dropwise with 42.8 g (0.246 mol) of diethyl azodicarboxylate. The mixture was heated to about 90° C. for about 6 hrs and then stirred overnight at RT. The solvent was evaporated and the residue was diluted with 500 mL of EtOAc, washed with water (1×400 mL), 1 N NaOH solution (2×400 mL), brine (1×400 mL), dried (MgSO₄), and evaporated to 119 g of a brown oil. Purification by flash chromatography (750 g of silica gel) using an EtOAc-hexane (3:7) eluant afforded 29.8 g (61%) of an oil. ¹H NMR (CDCl₃): δ 1.42–1.92 (6 H, m), 2.61 (2 H, t, J=7), 3.91 (3 H, s), 4.03 (2 H, t, J=7), 6.91 (1 H, d, J=8), 7.10–7.40 (m, 7 H), 9.77 (s, 1 H).

To a solution of 29.8 g (0.100 mol) of the above aldehyde in 300 mL of 95% ethanol was added 13.7 g (0.197 mol) of hydroxylamine hydrochloride in 100 mL of water followed by 16.6 g (0.197 mol) of sodium bicarbonate in small portions (gas evolution!). The mixture was stirred for about 4 h at RT and the ethanol was removed by evaporation. The residue was diluted with 250 mL of water and extracted with EtOAc (2×200 mL). The combined extracts were dried (MgSO₄) and evaporated to a yellow oil which was crystallized from hexane/ether to afford 15.0 g of the title compound, mp 65°–67° C. ¹H NMR (CDCl₃): δ 1.46–1.93 (6 H, m), 2.62 (2 H, t, J=7), 3.88 (3 H, s), 4.02 (2 H), J=7), 6.99–7.62 (m, 6 H), 7.49 (1 H, s), 8.04 (1 H, s).

An additional 2.00 g of product was obtained as a second crop from the filtrate, mp 67°–69° C. Evaporation of the filtrate and purification of the residue by flash chromatography using an EtOAc-hexane (2:3) eluant also provided an additional 4.18 g of product, mp 64°–66° C.

PREPARATIONS 2–4

The following compounds having the formula shown below were prepared, substantially according to the procedure of Preparation 1, substituting the indicated phenol for isovanillin and the indicated alcohol for 5-phenyl-1-pentanol. Compounds that were oils were purified by flash chromatography.

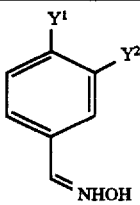

| Prep # | Y¹ | Y² | Phenol | Alcohol | M.P. (°C.) | ¹H NMR (CDCl₃) δ: |
|---|---|---|---|---|---|---|
| 2 | —OMe | —O-cyclopentyl | isovanillin | cyclopentanol | oil | 1.50–2.02 (8H, m), 3.94 (3H, s), 4.62–4.80 (1H, m), 6.91 (1H, d, J=8), 6.97 (1H, dd, J=8 and 1), 7.17 (1H, d, J=1), 8.02 (1H, s), 8.16 (1H, s) |
| 3 | H | —O-cyclopentyl | m-hydroxy-benzaldehyde | cyclopentanol | oil | 1.50–1.95 (8H, m), 4.7 4.78 (1H, m), 6.88 (1H, dd, J=3, 8), 7.05–7.28 (3H, m), 8.09 (1H, s), 8.43 (1H, s) |
| 4 | —O-cyclopentyl | —OMe | vanillin | cyclopentanol | 110–111 | 1.55–2.02 (8H, m), 3.88 (3H, s), 4.78–4.88 (1H, m), 6.86 (1H, d, J=8), 7.01 (1H, dd, J=2, 8), 7.21 (1H, d, J=2), 7.65 (1H, s), 8.07 (1H, s) |

PREPARATIONS 5–6

The following compounds having the formula shown below were prepared by condensation of the indicated aldehyde with hydroxylamine hydrochloride, substantially according to the procedure of Preparation 1.

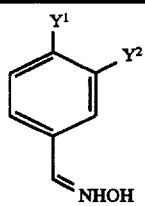

| Prep # | Y¹ | Y² | Aldehyde | M.P. (°C.) | ¹H NMR (DMSO-d₆) δ: |
|---|---|---|---|---|---|
| 5 | —OMe | —OH | isovanillin | 146–148 | 3.77 (3H, s), 6.92 (2H, s), 7.08 (1H, s), 7.96 (1H, s), 9.16 (1H, s), 10.90 (1H, s) |
| 6 | —OH | H | p-hydroxy-benzaldehyde | 115–118 | 6.77 (2H, d, J=9), 7.40 (2H, d, J=9), 8.00 (1H1 s), 9.74 (1H, s), 10.83 (1H, s) |

PREPARATION 7

Ethyl 2-Methylenebutyrate

A mixture of 5.0 g (0.019 mol) of triethyl 2-phosphonobutyrate, 5.5 g (0.039 mol) of K₂CO₃, 6.2 g (0.076 mol) of 37% aqueous formaldehyde solution, and 15 mL of water was heated to about 80° C. for about 45 min. After cooling to RT, 75 mL of ether was added and the organic layer was separated, washed with brine (1×20 mL), dried (MgSO₄), and filtered. The ether was carefully removed by distillation, leaving behind 2.1 g (87%) of the title compound as a clear oil which was used directly without further purification. ¹ H NMR (CDCl₃): δ 1.01 (3 H, t, J=7), 1.24 (3 H, t, J=7), 2.26 (2 H, q, J=7), 4.14 (2 H, q, J=7), 5.45 (1 H, s), 6.06 (1 H, s).

PREPARATION 8

3-[4-Methoxy-3-(5-phenylpentyloxy)]phenyl-2-isoxazoline-5-carboxylic Acid Ethyl Ester To a mixture of 1.28 g (9.57 mmol) of N-chlorosuccinimide, 200 μl of pyridine, and 200 mL of CH₂Cl₂ was added 2.00 g (6.38 mmol) of the compound of Preparation 1 in a solution of 15 mL of CH₂Cl₂. An exotherm was observed after about 10 min and following about 2 h of stirring at RT, 644 mg (698 μl, 6.38 mmol) of ethyl acrylate was added followed by 966 mg (1.33 ml, 9.57 mmol) of triethylamine. After the exotherm subsided, the mixture was stirred for about 2 h at RT. The mixture was diluted with 250 mL of $CH_2Cl_2$ and washed with aqueous 1 N HCl solution, sat'd. aqueous $NaHCO_3$ solution, dried ($Na_2SO_4$), and evaporated to an oil. Purification by flash chromatography (100 g of a silica gel) using an EtOAc-hexane (2:3) eluant afforded 1.82 g (69%) of the title compound as an oil. $^1$H NMR ($CDCl_3$): δ 1.29 (3 H, t, J=7), 1.40–1.91 (6 H, m), 2.60 (2 H, t, J=7), 3.55–3.58 (2 H, m), 3.95 (3 H, s), 3.99 (2 H, t, J=7), 4.22 (2 H, q, J=7), 5.05–5.12 (1 H, m), 6.79 (1 H, d, J=8), 6.95–7.31 (7 H, m).

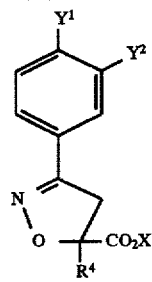

| Prep # | $Y^1$ | $Y^2$ | $R^4$ | X | Oxime | Olefin | M.P. (°C.) | $^1$H NMR ($CDCl_3$) δ or Elemental Analysis: |
|---|---|---|---|---|---|---|---|---|
| 9 | —OMe | $O(CH_2)_5$-Ph | Et | Et | Compound of Preparation 1 | Compound of Preparation 7 | oil | 0.98 (3H, t, J=7), 1.30 (3H, t, J=7), 1.48–2.03 (8H, m), 2.62 (2H, t, J=7), 3.18 (1H, d, J=17), 3.76 (1H, d, J=17), 3.86 (3H, s), 4.01 (2H, q, J=7), 6.82 (1H, d, J=8), 7.01 (1H, dd, J=2, 8), 7.15–7.33 (6H, m) |
| 10 | —OMe | —O-cyclopentyl | H | Et | Compound of Preparation 2 | Ethyl acrylate | oil | 1.27 (3H, t, J=7), 1.45–2.00 (8H, m), 3.66 (2H, d, J=10), 3.82 (3H, s), 4.22 (2H, q, J=7), 4.72–4.80 (1H, m), 5.09 (1H, t, J=10), 6.78 (1H, d, J=8), 6.98 (1H, d, J=8), 7.32 (1H, s) |
| 11 | —OMe | —O-cyclopentyl | H | Me | Compound of Preparation 2 | Methyl acrylate | 101–102 | 1.45–2.00 (8H, m), 3.56 (2H, d, J=10), 3.82 (3H, s), 3.87 (3H, s), 5.16 (1H, t, J=10), 6.82 (1H, d, J=8), 7.03 (1H, dd, J=2, 8), 7.37 (1H, d, J=2) |
| 12 | —OMe | —O-cyclopentyl | Me | Et | Compound of Preparation 2 | Ethyl methacrylate | 77–79 | 1.25 (3H, t, J=7), 1.50–2.00 (8H, m), 1.63 (3H, s), 3.11 (1H, d, J=17), 3.78 (1H, d, J=17), 3.91 (3H, s), 4.18 (2H, q, J=7), 4.68–4.77 (1H, m), 6.75 (1H, d, J=8), 6.92 (1H, dd, J=8, 2), 7.27 (1H, d, J=2) |
| 13 | H | —O-cyclopentyl | H | Me | Compound of Preparation 3 | Methyl acrylate | oil | 1.45–1.95 (8H, m), 3.55–3.58 (2H, m), 3.85 (3H, s), 4.65–4.74 (1H, m), 5.09 (1H, t, J=9), 6.85 (1H, dd, J=2, 8), 7.07 (1H, d, J=8), 7.12–7.22 (2H, m) |
| 14 | —O-cyclopentyl | OMe | H | Me | Compound of Preparation 4 | Methyl acrylate | oil | 1.45–1.95 (8H, m), 3.58–3.62 (2H, m), 3.79 (3H, s), 3.85 (3H, s), 4.65–4.74 (1H, m), 5.14 (1H, t, J=9), 6.83 (1H, d, J=9), 7.00 (1H, dd, J=2, 8), 7.34 (1H, d, J=2) |
| 15 | —OMe | —OH | H | Me | Compound of Preparation 5 | Methyl acrylate | 75–95 | 3.56–3.60 (2H, m), 3.79 (3H, s), 3.90 (3H, s), 5.12 (1H, t, J=10), 5.66 (1H, s), 6.83 (1H, d, J=9), 7.13 (1H, dd, J=2, 9), 7.24 (1H, d, J=2)* |
| 16 | —OH | H | H | Me | Compound of Preparation 6 | Methyl acrylate | 149–153 | 3.61–3.65 (2H, m), 3.83 (3H, s), 5.17 (1H, t, J=9), 5.80 (1H, bd s), 6.88 (2H, d, J=9), 7.56 (2H, d, J=9) |
| 17 | H | H | H | Et | Benzaldehyde oxime | Ethyl acrylate | 40–41 | 1.50 (3H, t, J=7), 3.60–3.65 (2H, m), 4.26 (2H, q, J=7), 5.15 (1H, t, J=9), 7.37–7.42 (3H, m), 7.64–7.70 (2H, m) |
| 18 | OMe | —O-cyclopentyl | Pr | Et | Compound of Preparation 2 | Compound of Prep. 34 | oil | 0.94 (3H, t, J=8), 1.30 (3H, t, J=8), 1.32–1.99 (12H, m), 3.20 (1H, d, J=17), 3.76 (1H, d, J=17), 3.85 (3H, s), 4.18–4.32 (2H, m), 4.72–4.82 (1H, m), 6.82 (1H, d, J=8), 7.00 (1H, dd, J=2 and 8), 7.34 (1H, d, J=2) |
| 19 | OMe | —O-cyclopentyl | Bu | Et | Compound of Preparation 2 | Compound of Prep. 35 | 53–36 | 0.90 (3H, t, J=8), 1.30 (3H, t, J=8), 1.22–1.98 (14H, m), 3.20 (1H, d, J=17), 3.78 (1H, d, J=17), 3.86 (3H, s), 4.20–4.29 (2H, m), 4.75–4.85 (1H, m), 6.82 (1H, d, J=8), 7.01 (1H, dd, J=2 and 8), 7.34 (1H, d, J=2) |

-continued

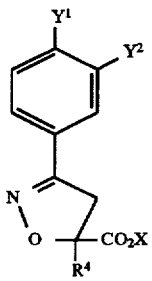

| Prep # | Y¹ | Y² | R⁴ | X | Oxime | Olefin | M.P. (°C.) | ¹H NMR (CDCl₃) δ or Elemental Analysis: |
|---|---|---|---|---|---|---|---|---|
| 20 | OMe | —O-cyclopentyl | Ph | Et | Compound of Preparation 2 | Compound of Prep. 36 | 98–100 | Anal. Calc'd for: $C_{24}H_{27}NO_5$: C, 70.39; H, 6.65; N, 3.42. Found: C, 70.30, H, 6.81; N, 3.56 |
| 21 | \[structure with OMe, O-cyclopentyl, N-O, CO₂Me\] | | | | Compound of Preparation 2 | Methyl 1-cyclo-pentenoate | oil | 1.60–2.37 (14H, m), 3.79 (3H, s), 3.86 (3H, s), 4.21 (1H, dd, J=3 and 7), 4.75–4.80 (1H, m), 6.82 (1H, d, J=9), 7.05 (1H, dd, J=2 and 9), 7.34 (1H, J=2) |

*The NMR shows a contaminant which is most likely a product resulting from chlorination of the aromatic ring.

PREPARATION 22

3-(3,4-Dimethoxyphenyl)-2-isoxazoline-5-carboxylic Acid Methyl Ester

To a solution of 1.5 g (6.00 mmol) of the compound of Preparation 15 in 25 mL of DMF was added 91 0 mg of $K_2CO_3$ (6.60 mmol) and 0.41 mL (940 mg, 6.6 mmol) of methyl iodide. The mixture was heated to about 50° C. and the progress of the reaction was monitored by TLC. Additional 0.4 mL portions of methyl iodide were added at about 1 and 2 h, respectively. After about 2 h of additional heating, the reaction was cooled, diluted with 250 mL of water, extracted with EtOAc (3×100 mL), dried (MgSO₄), and evaporated to an oil. Purification by flash chromatography using an EtOAc-hexane (1:3) eluant afforded 270 mg of the title compound, mp 106°–108° C. ¹H NMR (CDCl₃): δ 3.59–3.63 (2 H, m), 3.79 (3 H, s), 3.89 (3 H, s), 5.15 (1 H, t, J=8), 6.83 (1 H, d, J=8), 7.03 (1 H, dd, J=2, 8), 7.37 (1 H, d, J=8); MS (m/e): 266 (M⁺+1).

PREPARATIONS 23–25

The following compounds having the formula shown below were prepared, substantially according to the procedure of Preparation 22, substituting the indicated phenol for that of Preparation 15 and the indicated alkylating agent for methyl iodide.

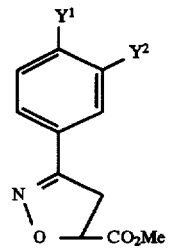

| Prep # | Y¹ | Y² | Phenol | Alkylating Agent | M.P. (°C.) | Data |
|---|---|---|---|---|---|---|
| 23 | OMe | OBn | Cmpd of Prep 15 | PhCH₂Br | 183–185 | ¹H NMR (CDCl₃): δ 3.54–3.58 (2H, m), 3.79 (3H, s), 3, 89 (3H, s), 5.10–5.26 (1H, m), 5.13 (2H, s), 6.86 (1H, d, J=9), 7.06 (1H, dd, J=2, 8), 7.32–7.40 (6H, m); |

-continued

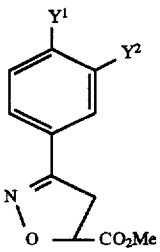

| Prep # | Y¹ | Y² | Phenol | Alkylating Agent | M.P. (°C.) | Data |
|---|---|---|---|---|---|---|
| 24 | quinoline-CH₂O— | H | Cmpd of Prep 16 | quinoline-CH₂Cl | 112–113 | MS 9m/e): 342 (M⁺+ 1)<br>¹H NMR (CDCl₃): δ 3.56–3.59 (2H, m), 3.78 (3H, s), 5.12 (1H, t, J=8), 5.34 (2H, s), 7.02 (2H, d, J=9), 7.54–7.82 (6H, m), 8.06 (1H, d, J=8), 8.17 (1H, d, J=8); MS (m/e): 363 (M⁺+ 1) |
| 25 | —OCH₂Ph | H | Cmpd of Prep 16 | PhCH₂Br | 127–128 | Anal. Calc'd for $C_{18}H_{17}NO_4$: C, 69.43; H, 5.50; N, 4.50. Found: C, 69.18; H, 5.31; N, 4.59 |

PREPARATION 26

[3aR-(3aα,6α,7aβ)]-Hexahydro-8,8-dimethyl-1-(1-oxo-2-propenyl)-3H-3a,6-methano-2,1-benzisothiazole 2,2-Dioxide The title compound was prepared according to the method of Curran and Heffner (Curran, D. P., Heffner, T. A., *J. Org. Chem.*, 1990, 55, 4585) starting with (+)-L-2,10-camphor suitam, which was purchased from Fluka.

Into a 1 L 3-neck round bottom flask fitted with reflux condenser, N₂ inlet, rubber septum and glass stopper was placed 4.03 g (0.084 mol) of 50% NaH dispersion, 400 mL of toluene, and 12.0 g (0.056 mol) of (+)-10,2-camphor suitam. After stirring for 1 h. at RT, 594 mg (0.006 mol) of CuCl followed by 9.10 mL (0.056 mol) of acryloyl chloride were added and stirring was continued overnight at RT. The mixture was then treated with 15 mL of water, evaporated, diluted with water (200 mL), and extracted with EtOAc (3×200 mL). The combined extracts were dried (MgSO₄) and evaporated to a solid. Purification by flash chromatography (1 kg of silica gel) using a 3:7 EtOAc-hexane eluant afforded a white solid which was triturated with ether to provide 7.4 g of the title compound, mp 179°–182° C.

PREPARATION 27

[3aS-(3aα,6α,7aβ)]-Hexahydro-8,8-dimethyl-1-(1-oxo-2-propenyl)-3H)-3a,6-methano-2,1-benzisothiazole 2,2-Dioxide The title compound was prepared according to the procedure of Preparation 26, however, starting with (–)-D-2,10-camphor suitam, which was purchased from Fluka.

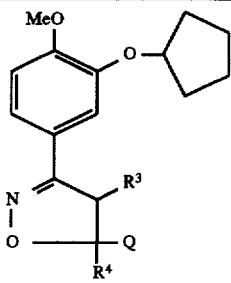

| Prep. | R³ | R⁴ | Q | Olefin | MP (°C.) | $[\alpha]_D^{25}$ CHCl₃ | Data |
|---|---|---|---|---|---|---|---|
| 28ᵃ | H | H | ![structure with N-SO2 and acetyl group on bicyclic] | Compound of Prep. 26 | foam | +187° | ¹H-NMR(CDCl₃): δ 0.97 (3H, s), 1.19 (3H, s), 1.28–2.22 (15H, m), 3.41–3.95 (5H, m), 3.85 (3H, s), 4.74–4.82 (1H, m), 5.63 (1H, dd, J=8, 10), 6.80 (1H, d, J=8), 7.02 (1H, dd, J=2, 8), 7.33 (1H, d, J=2). |
| 29ᵃ | H | H | ![structure with N-SO2 and acetyl group on bicyclic] | Compound of Prep. 27 | foam | +46° | ¹H-NMR(CDCl₃): δ 0.94 (3H, s), 1.17 (3H, s), 1.25–2.21 (15H, m), 3.39–3.93 (5H, m), 3.83 (3H, s), 4.73–4.81 (1H, m), 5.61 (1H, dd, J=8, 10), 6.79 (1H, d, J=8), 7.01 (1H, dd, J=2, 8), 7.32 (1H, d, J=2). |
| 30 | H | H | (CH₂)₂OH | CH₂=CH(CH₂)₂OH | 89–91 | racemic | Anal. Calc'd. for C₁₇H₂₃NO₄: C, 66.86; H, 7.59; N, 4.59. Found: C, 66.71; H, 7.77; N, 4.64. |
| 31ᵇ | H | Me | CO₂Me | ethyl crotonate | oil | racemic | ¹H-NMR(CDCl₃): 1.40–2.05 (8H, m), 1.43 (3H, d, J=7), 3.69 (3H, s), 3.84 (3H, s), 4.01 (1H, d, J=7), 4.74–4.82 (1H, m), 4.95–5.06 (1H, m), 6.79 (1H, d, J=8), 7.05 (1H, dd, J=2, 8), 7.31 (1H, d, J=2). |

ᵃless polar diastereomer (R_f 0.61; 1:1 ether:toluene); ᵇtrans stereochemistry

PREPARATION 32

3-(3-Cyclopentyloxy-4-methoxy)phenyl-2-isoxazoline-5-acetic Acid

To a solution of 1.85 g (6.06 mmol) of the compound of Preparation 30 in 50 mL of acetone chilled to about 0° C. in an ice bath was added dropwise 9.70 mL (12.1 mmol) of a 1.25 M solution of Jones reagent. The ice bath was allowed to melt, and after about 4 h. of stirring an additional 2.00 mL of Jones reagent was added and stirring was continued overnight. Excess reagent was quenched by the addition of 10 mL of isopropanol, and the solids were removed by filtration. The filtrate was concentrated and the residue was taken up in 150 mL of EtOAc, washed with water (2×100 mL), dried (MgSO₄), and evaporated to a yellow oil. Crystallization from ether-hexane gave 1.06 g of the title compound, mp 123°–126° C.
¹H-NMR (CDCl₃): δ 1.55–2.06 (8 H, m), 2.66–3.59 (4 H, m), 3.87 (3 H, x), 4.78–4.87 (1 H, m), 5.02–5.15 (1 H, m), 6.84 (1 H, d, J=8), 7.02 (1 H, dd, J=1, 8), 7.37 (1 H, d, J=2).

PREPARATION 33

3-(3-Cyclopentyloxy-4-methoxy)phenyl-2-isoxazoline-5-acetic Acid Methyl Ester

A solution of 530 mg of the compound of Preparation 32 in 5 mL of MeOH was saturated with HCl gas and the mixture was stirred for about 3 h. at RT protected from atmospheric moisture with a CaCl₂ tube. The mixture was concentrated and the residue was taken up in 50 mL of EtOAc, washed with saturated aqueous NaHCO₃ solution (2×50 mL), dried (MgSO₄), and evaporated to 530 mg of an oil. Purification by flash chromatography (25 g of silica gel) using a 2:3—EtOAc:hexane eluant gave an oil which was crystallized from hexane-ether to afford 323 mg of the title compound as a white solid, mp 78°–80° C.

Anal. Calc'd. for C₁₈H₂₃NO₅: C, 64.85; H, 6.95; N, 4.20. Found: C, 64.49; H, 7.08; N, 4.13.

PREPARATIONS 34–36

The following compounds having the formula shown below were prepared as oils substantially according to the procedure of Preparation 7 substituting the indicated ester for triethylphosphonobutyrate.

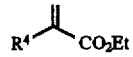

| Prep. # | R⁴ | Ester | ¹H-NMR(CDCl₃): δ |
|---|---|---|---|
| 34 | Pr | triethyl phosphonopentanoate | 0.90 (3H, t, J=7), 1.28 (3H, t, J=7), |

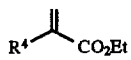

| Prep. # | R⁴ | Ester | ¹H-NMR(CDCl₃): δ |
|---|---|---|---|
| 35 | Bu | triethyl phosphonohexanoate | 1.40–1.53 (2H, m), 2.25 (2H, dt, J=1 and 7), 4.17 (2H, q, J=7), 5.48 (1H, q, J=1), 6.11 (1H, t, J=11) 0.90 (3H,t, J=7), 1.29 (3H, t, J=7), 1.26–1.48 (4H, m), 2.28 (2H, t, J=7), 4.19 (2H, q, J=7), 5.49 (1H, q, J=1), 6.11 (1H, t, J=1) |
| 36 | Ph | triethyl phosphonophenylacetate | 1 .32 (3H, t, J=7), 4.28 (2H, q, J=7), 5.88 (1H, d, J=1), 6.34 (1H, d, J=1), 7.20–7.45 (5H, m) |

PREPARATIONS 37 and 38

Less Polar Diastereomer of N-[(S)-α-Methylbenzyl]-3-(3-cyclopentyloxy-4-methoxy)phenyl-5-methyl-2-isoxazoline-5-carboxamide (Preparation 37)

More Polar Diastereomer of N-[(S)-α-Methylbenzyl]-3-(3-Cyclopentyloxy-4-methoxy)phenyl-5-methyl-2-isoxazoline-5-carboxamide (Preparation 38)

A solution of 5.00 g (14 mmol) of the compound of Preparation 12 in 100 mL of absolute ethanol was treated with 2.36 g (42 retool) of KOH and the mixture was stirred for about 4 hr at RT. An additional equivalent of KOH was added and stirring was continued for about 3 days. The mixture was concentrated, diluted with water, acidified with aqueous 1 N HCl solution, and extracted with EtOAc (2×100 mL). The combined extracts were dried (MgSO₄), evaporated, and triturated with hexane-ether to give 3.46 g of 3-[3-cyclopentyloxy-4-methoxy]phenyl-5-methyl-2-isoxazoline-5-carboxylic acid, mp 153°–154°.

A mixture of 3.00 g (94 mmol) of the above compound, 100 mL of benzene, and 2.46 mL (28.2 mmol) of oxalyl chloride was heated to reflux for about 3 hr. The mixture was concentrated, diluted with 100 mL of CH₂Cl₂, and treated with 2.42 mL (18.8 mmol) of S-(−)-α-methylbenzylamine. After stirring for about 16 hr at RT, the mixture was concentrated, diluted with 200 mL of EtOAc, washed with aqueous 1 N HCl solution (2×100 mL), saturated aqueous NaHCO₃ solution (2×100 mL), dried (Na₂SO₄), and evaporated. The residual solid (5.76 g) was purified by flash chromatography over 600 g of silica gel using 15–20% ether-toluene as eluant. Following a 500 mL pre-fraction, 35 ml-fractions were collected. Fractions 59–68 were pooled and evaporated to give 630 mg of the compound of Preparation 37, mp 154°–156° C.; R_f=0.20, 20% ether-toluene. Anal. calculated for C₂₅H₃₀N₂O₄: C, 71.06; H, 7.16; N, 6.63. Found: C, 71.13; H, 7.42; N, 6.76.

Fractions 82–104 were pooled and concentrated to 720 mg of a white solid which was triturated with hexane-ether to give 596 mg of a white solid, mp 165°–167° C. Recrystallization from ether-CH₂Cl₂ afforded 435 mg of the compound of Preparation 38, mp 167°–168° C. An additional 1.03 g of the compound of Preparation 38, mp 166°–167° C., was obtained by recrystallization (ether-CH₂Cl₂) of the combined evaporated residues of the mother liquor and Fractions 69–81. Anal. calculated for C₂₅H₃₀N₂O₄: C, 71.06; H, 7.16; N, 6.63. Found: C, 70.89; H, 7.40; N, 6.77.

PREPARATION 39

(+)-3-(3-Cyclopentyloxy-4-methoxy)phenyl-5-methyl-2-isoxazoline-5-carboxylic Acid Methyl Ester Into a flame-dried, 3-neck round-bottom flask under N₂ was placed a suspension of 549 mg (3.56 mmol) of 26% KH in mineral oil. After removal of the mineral oil by 2 successive hexane washes, the bare hydride was suspended in 35 mL of THF and a solution of 750 mg (1.78 mmol) of the compound of Preparation 37 in 35 mL of dry THF was added dropwise. After the bubbling subsided, 161 µl (2.67 mmol) of carbon disulfide was added. The mixture was stirred for about 16 hr at RT and was quenched by the addition of 6 mL of water. The THF was evaporated and the residue was diluted with saturated aqueous NaHCO₃ solution and washed with EtOAc (2×100 mL). The aqueous layer was acidified to pH 3 with aqueous 6 N HCl solution, extracted with EtOAc (2×100 mL), dried (MgSO₄), and evaporated to 217 mg of an orange oil.

A solution of the above oil in 20 mL of MeOH was saturated with HCl gas and stirred for about 16 hr at RT. The mixture was concentrated, diluted with 50 mL of EtOAc, dried (MgSO₄), and evaporated to a yellow solid. Purification by flash chromatography over 12 g of silica gel using a 60% EtOAc-hexane eluant afforded 131 mg of the title compound after trituration in hexane-ether, mp 127°–128° C. [α]_C²⁵+100° (c=0.64, CHCl₃). Anal. calculated for C₁₈H₂₃NO₅·¼H₂O: C, 63.99; H, 7.01; N, 4.15. Found C, 64.03; H, 6.96; N, 4.15.

PREPARATION 40

(−)-3-(3-Cyclopentyloxy-4-methoxy)phenyl-5-methyl-2-isoxazoline-5-carboxamide

The title compound was prepared substantially according to Procedure 39 substituting the compound of Preparation 38 for the compound of Preparation 37; mp 124°–125° C.; [α]_C²⁵−101° (c=0.61, CHCl₃). Anal. calculated for C₁₈H₂₃NO₅·¼H₂O; C, 63.99; H, 7.01; N, 4.15. Found: C, 64.04; H, 7.00; N, 4.17.

What is claimed is:

1. A compound of the formula

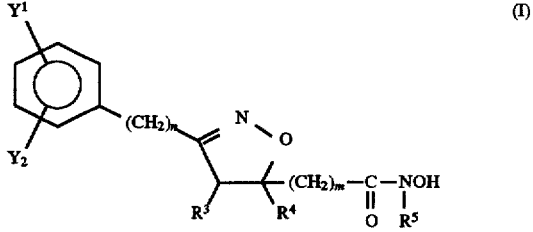

(I)

the racemic, racemic-diastereomeric mixtures and optical isomers of said compounds and the pharmaceutically acceptable salts thereof wherein m is 0, 1, 2 or 3;

n is 0, 1, 2 or 3;

Y¹ and Y² are independently selected from the group consisting of hydrogen, (C₁–C₆) alkyl, optionally substituted phenylalkyl having 1 to 6 carbons in the alkyl portion, optionally substituted phenoxyalkyl having 1 to 6 carbons in the alkyl portion, $(C_3-C_7)$cycloalkyl, difluoromethyl, trifluoromethyl, fluoro, chloro, bromo, iodo, —$OR^1$ and —$OR^2$;

wherein the aromatic portion of the optionally substituted phenylalkyl, and the aromatic portion of the optionally substituted phenoxyalkyl are optionally independently substituted with $(C_1-C_4)$alkyl, $(C_1-C_4)$alkoxy, halogen or $CF_3$; $R^1$ is $(C_1-C_4)$alkyl, phenylalkyl having one to four carbon atoms in the alkyl portion, fluoromethyl, difluoromethyl, trifluoromethyl, or —$(CH_2)_q$-quinoline wherein q is 1, 2 or 3;

$R^2$ is $(C_1-C_3)$alkyl, $(C_3-C_7)$cycloalkyl, alkoxyalkyl having 3 to 7 carbons in the alkoxy portion and 2 and 4 carbons in the alkyl portion, optionally substituted phenoxyalkyl having 2 to 6 carbons in the alkyl portion, optionally substituted phenylalkyl having 1 to 6 carbons in the alkyl portion, bicycloalkyl having 6 to 9 carbons or optionally substituted indanyl;

wherein the aromatic portion of the optionally substituted phenylalkyl, the aromatic portion of the optionally substituted phenoxyalkyl and the optionally substituted indanyl are optionally substituted with $(C_1-C_4)$alkyl, $(C_1-C_4)$alkoxy, halogen or $CF_3$;

$R^3$ is hydrogen, $(C_1-C_3)$alkyl, fluoro$(C_1-C_3)$alkyl having 1 to 3 fluoro atoms, mono-hydroxyalkyl having 1 to 3 carbons or alkoxyalkyl having 1 to 3 carbons in the alkyl portion and 1 to 3 carbons in the alkoxy portion;

$R^4$ is hydrogen, $(C_1-C_5)$alkyl, fluoro$(C_1-C_5)$alkyl having 1 to 3 fluoro atoms, mono-hydroxyalkyl having 1 to 3 carbons, phenyl, alkoxyalkyl having 1 to 3 carbons in the alkyl portion and 1 to 3 carbons in the alkoxy portion, aminoalkyl having 1 to 3 carbons,

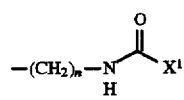

wherein $X^1$ is $(C_1-C_3)$alkyl and n is an integer from 1 to 3, N-alkylaminoalkyl having 1 to 3 carbons in the alkylamino portion and 1 to 3 carbons in the alkyl portion, $(C_3-C_7)$ cycloalkyl or N,N-dialkylaminoalkyl having a total of 2 to 6 carbons in the dialkylamino portion and 1 to 3 carbons in the alkyl portion; $R^5$ is hydrogen or $(C_1-C_3)$alkyl;

or $R^3$ and $R^4$ are taken together with the carbon atoms to which they are attached and form a carbocyclic ring having 4 to 7 carbon atoms provided that when $R^3$ is hydrogen, $R^4$ is hydrogen, $R^5$ is hydrogen, m is 1 and n is 0 then $Y^1$ and $Y^2$ are not fluoro, chloro, bromo, or iodo.

2. A compound according to claim 1 or a pharmaceutically acceptable salt thereof wherein $Y^1$ is —$OR^1$ and is attached to the 4-position of the phenyl ring and $Y^2$ is —$OR^2$ and is attached to the 3-position of the phenyl ring.

3. A compound according to claim 2 or a pharmaceutically acceptable salt thereof wherein $R^1$ is $(C_1-C_4)$alkyl, phenylalkyl having one to four carbon atoms in the alkyl portion or —$(CH_2)_q$-quinoline; m is 0 and n is 0.

4. A compound according to claim 3 or a pharmaceutically acceptable salt thereof wherein $R^2$ is phenylalkyl having 1 to 6 carbons in the alkyl portion, $(C_3-C_7)$cycloalkyl, or $(C_1-C_3)$alkyl.

5. A compound according to claim 4 or a pharmaceutically acceptable salt thereof wherein $R^2$ is 5-phenylpentyl, benzyl, cyclopentyl or methyl.

6. A compound according to claim 5 or a pharmaceutically acceptable salt thereof wherein $R^3$ is hydrogen.

7. A compound according to claim 6 or a pharmaceutically acceptable salt thereof wherein $R^4$ is hydrogen or $(C_1-C_5)$ alkyl.

8. A compound according to claim 7 or a pharmaceutically acceptable salt thereof wherein $R^5$ is hydrogen or $(C_1-C_3)$ alkyl.

9. A compound according to claim 8 or a pharmaceutically acceptable salt thereof wherein $R^1$ is methyl; $R^2$ is cyclopentyl; $R^4$ is hydrogen; and $R^5$ is hydrogen.

10. The levorotatory (negative rotation) enantiomer of the compound according to claim 9 or a pharmaceutically acceptable salt thereof.

11. A compound according to claim 8 or a pharmaceutically acceptable salt thereof wherein $R^1$ is methyl; $R^2$ is cyclopentyl; $R^4$ is methyl; and $R^5$ is hydrogen.

12. The levorotatory (negative rotation) enantiomer of the compound according to claim 11 or a pharmaceutically acceptable salt thereof.

13. A pharmaceutical composition comprising an effective amount of a compound according to claim 1 or a pharmaceutically acceptable salt thereof and a pharmaceutically acceptable diluent or carrier.

14. A method of inhibiting phosphodiesterase type IV in a mammal in need thereof which comprises administering to said mammal a phosphodiesterase type IV inhibiting amount of a compound according to claim 1 or a pharmaceutically acceptable salt thereof.

15. A method of treating an inflammatory condition in a mammal which comprises administering to said mammal an antiinflammatory amount of a compound according to claim 1 or a pharmaceutically acceptable salt thereof.

16. A method of treating asthma, arthritis, bronchitis, chronic obstructive pulmonary disease, psoriasis, allergic rhinitis, dermatitis or shock in a mammal which comprises administering to said mammal an effective amount of a compound according to claim 1 or a pharmaceutically acceptable salt thereof.

* * * * *